(12) United States Patent
Sgroi, Jr. et al.

(10) Patent No.: US 11,464,541 B2
(45) Date of Patent: Oct. 11, 2022

(54) RETAINING MECHANISMS FOR TROCAR ASSEMBLY

(71) Applicant: Covidien LP, Mansfield, MA (US)

(72) Inventors: Anthony Sgroi, Jr., Wallingford, CT (US); Justin Williams, Southbury, CT (US); Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 721 days.

(21) Appl. No.: 16/449,614

(22) Filed: Jun. 24, 2019

(65) Prior Publication Data

US 2020/0397475 A1   Dec. 24, 2020

(51) Int. Cl.
| | |
|---|---|
| *A61B 17/072* | (2006.01) |
| *A61B 17/34* | (2006.01) |
| *A61B 17/115* | (2006.01) |
| *A61B 17/068* | (2006.01) |
| *A61B 17/00* | (2006.01) |

(52) U.S. Cl.
CPC ........ *A61B 17/3462* (2013.01); *A61B 17/068* (2013.01); *A61B 17/1155* (2013.01); *A61B 17/3496* (2013.01); *A61B 2017/0046* (2013.01); *A61B 2017/00477* (2013.01); *A61B 2017/347* (2013.01)

(58) Field of Classification Search
CPC . A61B 17/068; A61B 17/1155; A61B 17/072; A61B 2017/07257
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |
| (Continued) | | |

FOREIGN PATENT DOCUMENTS

| | | |
|---|---|---|
| CA | 2451558 A1 | 1/2003 |
| CN | 1547454 A | 11/2004 |
| (Continued) | | |

OTHER PUBLICATIONS

Extended European Search Report corresponding to International Application No. EP 14 18 4882.0 dated May 12, 2015.

(Continued)

*Primary Examiner* — Gloria R Weeks
(74) *Attorney, Agent, or Firm* — Carter, DeLuca & Farrell LLP

(57) ABSTRACT

A retaining mechanism for releasably securing a trocar assembly within an outer sleeve of an adapter assembly includes a retaining block, a cam wire moveably positioned relative to the retaining block between a lock position and a release position, a retaining block extension maintaining the cam wire relative to the retaining block, a button member in operable engagement with the cam wire, and a pair of retaining members moveable from a first position received within first and second openings of the trocar assembly when the cam wire is in the lock position and a second position spaced from the trocar assembly when the cam wire is in the release position. The retaining members each define a cutout having first and second stepped cutout portions and a smooth transition between the first and second stepped cutouts for receiving the cam wire.

10 Claims, 15 Drawing Sheets

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,333,773 A * | 8/1994 | Main .................. A61B 17/115 227/19 |
| 5,350,104 A * | 9/1994 | Main .................. A61B 17/115 227/19 |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,945,444 B2 * | 9/2005 | Gresham .............. A61B 17/115 227/181.1 |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |

(56) References Cited

U.S. PATENT DOCUMENTS

| | | |
|---|---|---|
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,733,611 B2 * | 5/2014 | Milliman ............ A61B 17/115 227/175.2 |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,987,001 B2 * | 6/2018 | Williams ............ A61B 17/1155 |
| 11,147,561 B2 * | 10/2021 | Sgroi, Jr. ............... A61B 90/03 |
| 11,317,945 B2 * | 5/2022 | Williams et al. .. A61B 17/3468 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |

(56) References Cited

U.S. PATENT DOCUMENTS

| | | |
|---|---|---|
| 2004/0176751 A1 | 9/2004 | Weitzner et al. |
| 2004/0193146 A1 | 9/2004 | Lee et al. |
| 2005/0116009 A1* | 6/2005 | Milliman ............ A61B 17/1155 227/176.1 |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0284792 A1* | 10/2013 | Ma ..................... A61B 1/00087 227/176.1 |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0129636 A1* | 5/2015 | Mulreed ............... A61B 17/115 227/177.1 |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |

(56) References Cited

U.S. PATENT DOCUMENTS

| 2016/0113649 | A1 | 4/2016 | Zergiebel et al. | |
|---|---|---|---|---|
| 2016/0374667 | A1* | 12/2016 | Miller .................. | A61B 17/068 227/175.2 |
| 2021/0298755 | A1* | 9/2021 | Sgroi .................. | A61B 17/1155 |

FOREIGN PATENT DOCUMENTS

| CN | 1957854 | A | 5/2007 |
|---|---|---|---|
| CN | 101495046 | A | 7/2009 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1769754 | A1 | 4/2007 |
| EP | 2316345 | A1 | 5/2011 |
| EP | 2668910 | A2 | 12/2013 |
| EP | 3103402 | A1 | 12/2016 |
| EP | 3245959 | A2 | 11/2017 |
| ES | 2333509 | A1 | 2/2010 |
| JP | 2005125075 | A | 5/2005 |
| KR | 20120022521 | A | 3/2012 |
| WO | 2011108840 | A2 | 9/2011 |
| WO | 2012/040984 | A1 | 4/2012 |

OTHER PUBLICATIONS

Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report, dated Jan. 25, 2021, corresponding to European Application No. 20020295.0; 10 pages.

* cited by examiner

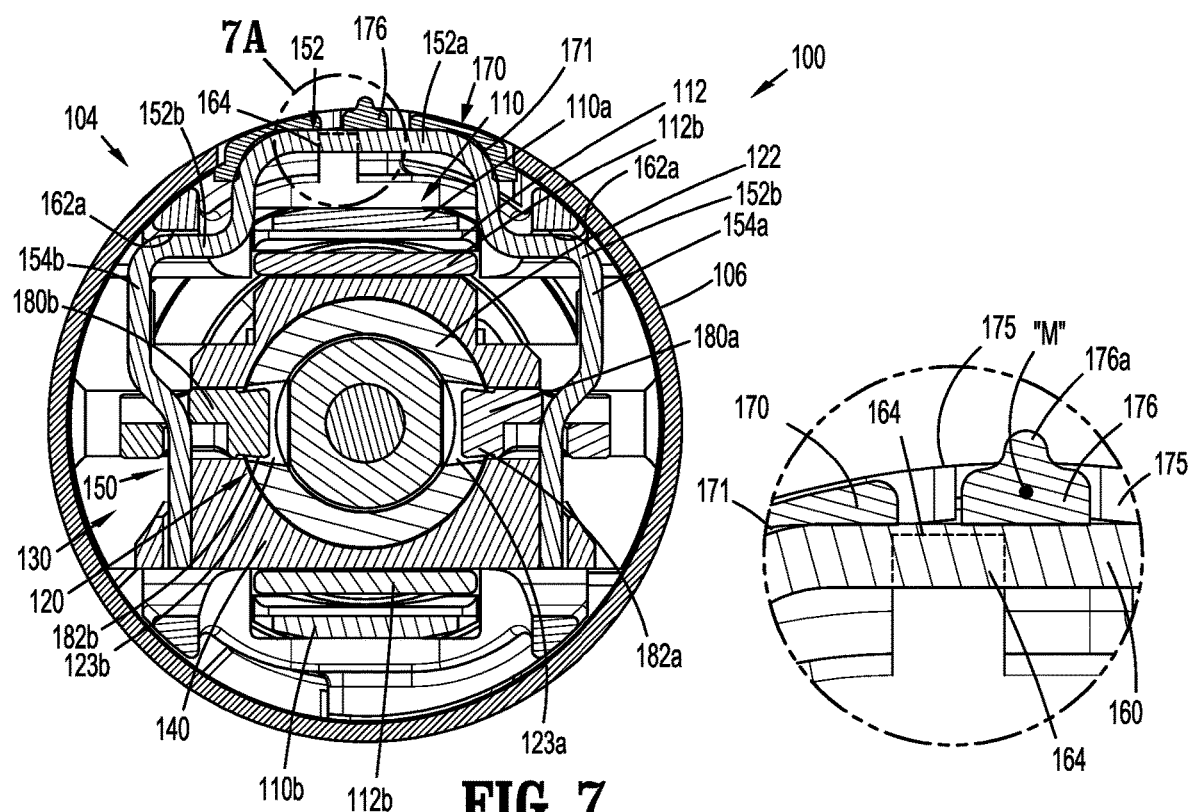
FIG. 7
FIG. 7A
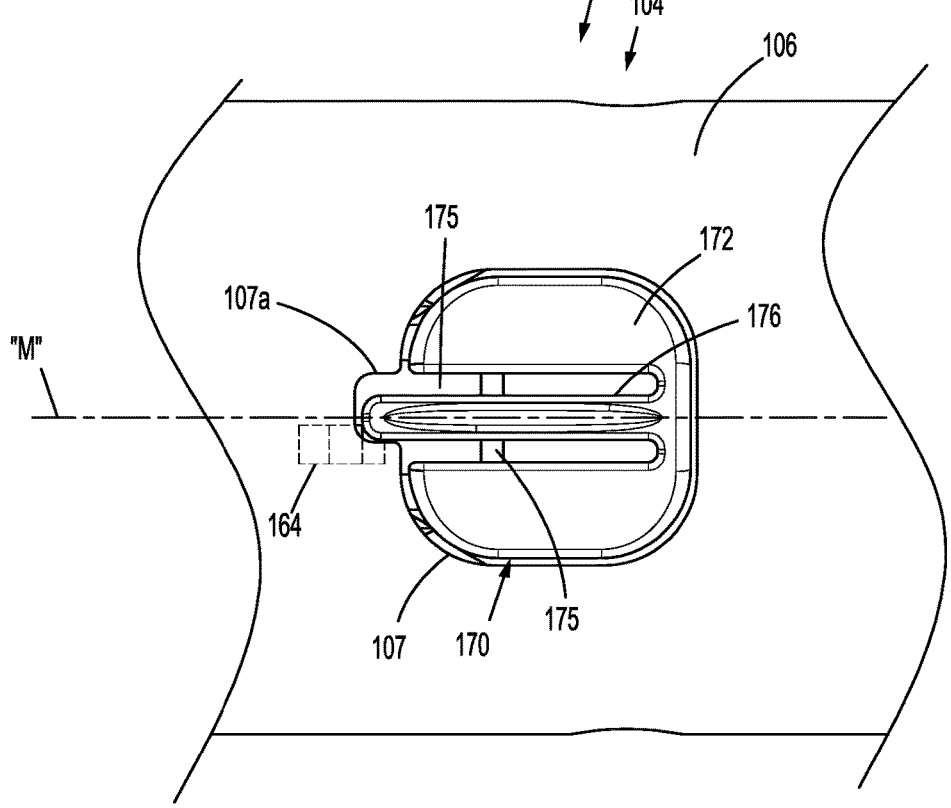
FIG. 8

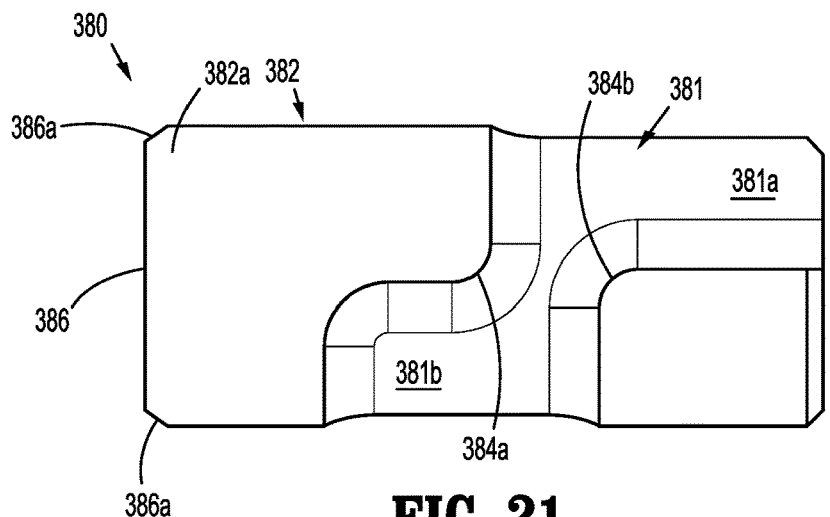
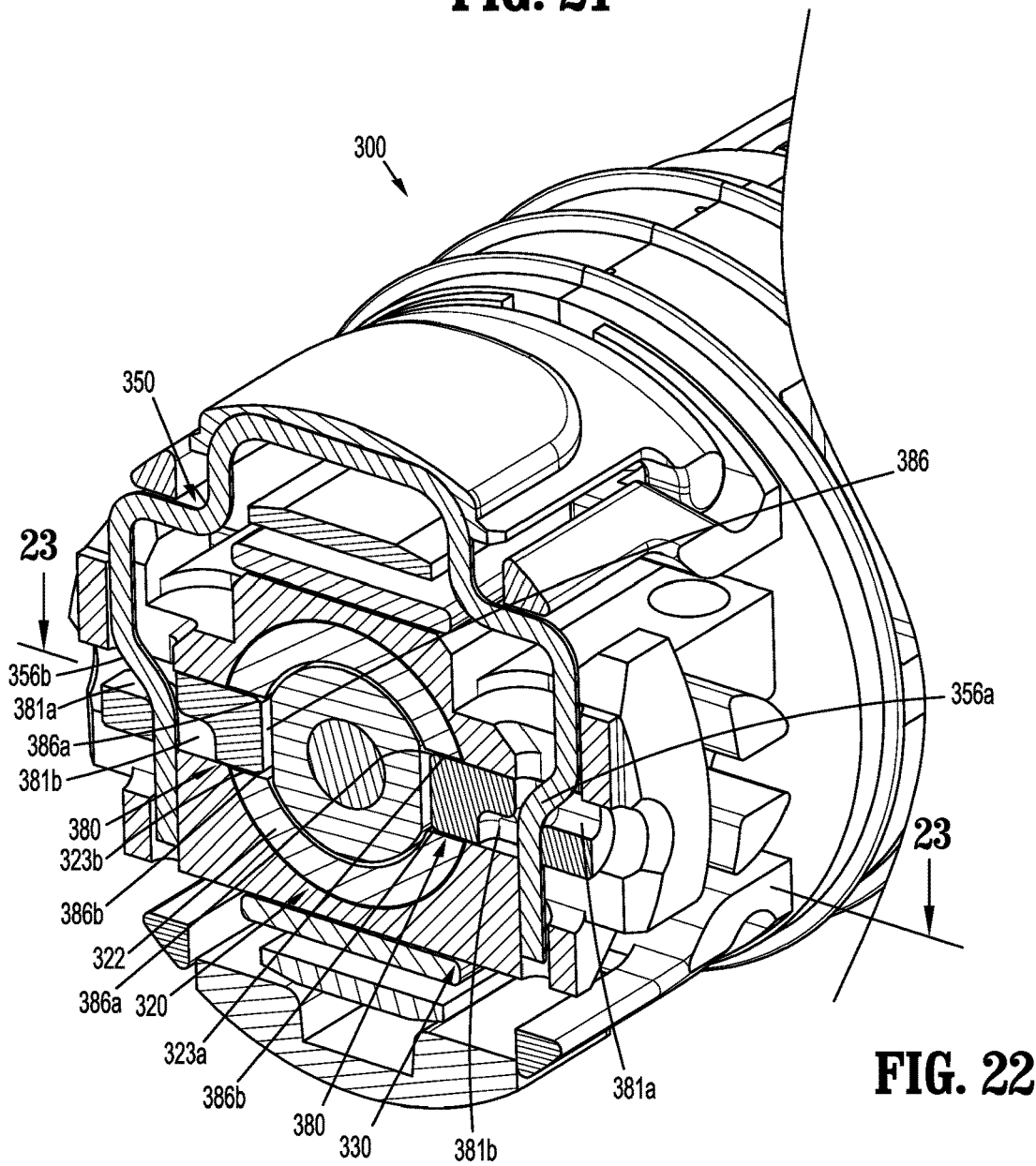
FIG. 21
FIG. 22

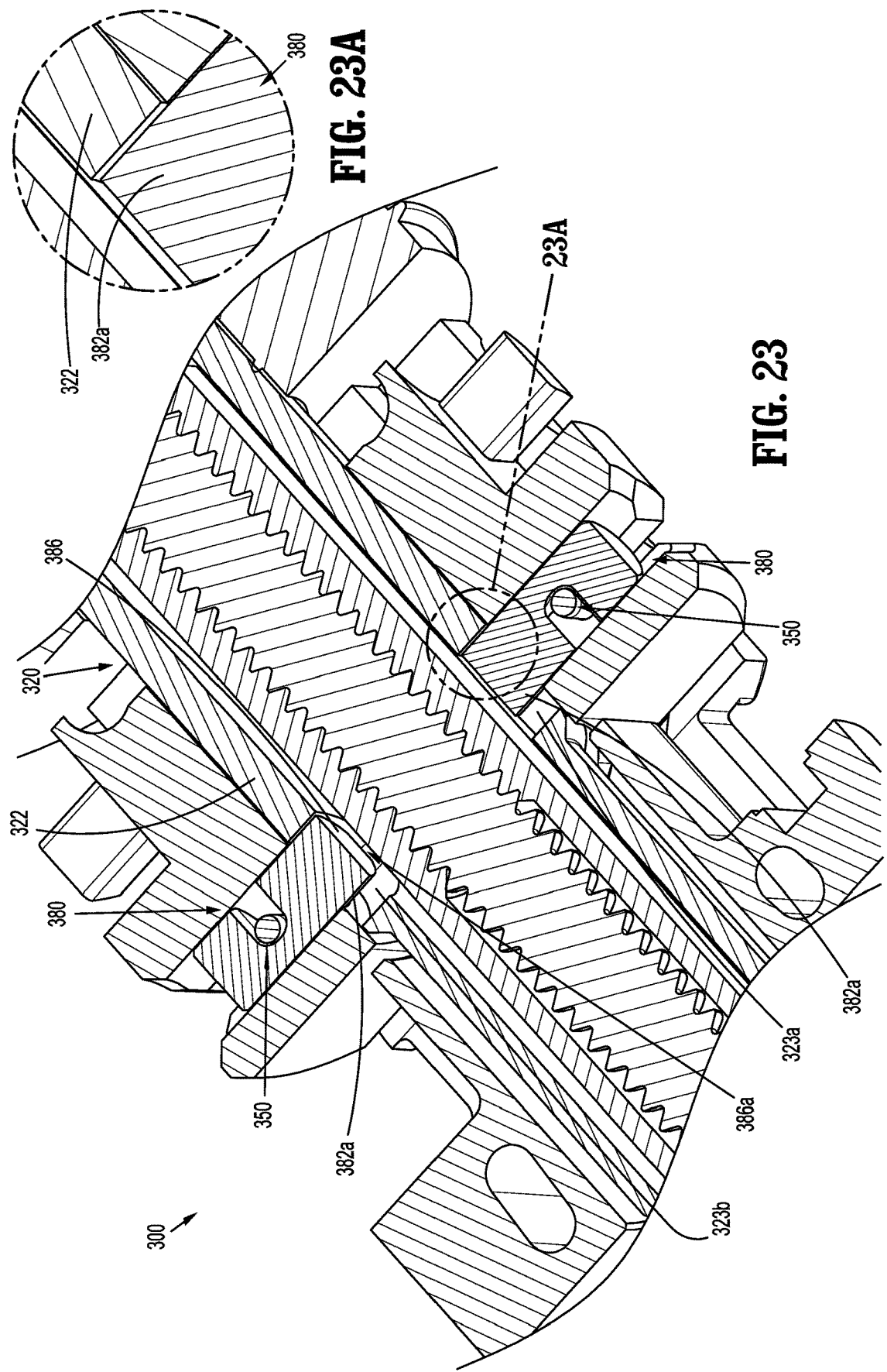

RETAINING MECHANISMS FOR TROCAR ASSEMBLY

FIELD

The present disclosure relates to reusable adapter assemblies for surgical stapling devices. More particularly, the present disclosure relates to a retaining mechanism for releasably securing a removable trocar assembly within a reusable adapter assembly.

BACKGROUND

Surgical devices for applying staples, clips, or other fasteners to tissue are well known. Typically, endoscopic stapling devices include an actuation unit, i.e., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly.

Circular stapling devices typically includes a trocar assembly for positioning an attached anvil assembly. The trocar assembly may be releasably securable within the adapter assembly to permit cleaning and sterilizing and reuse of the adapter assembly. It would be beneficial to have a retaining mechanism for releasably securing the trocar assembly with the adapter assembly.

SUMMARY

An adapter assembly for connecting a loading unit to a handle assembly includes an outer sleeve, a trocar assembly releasably securable with the outer sleeve, and a retaining mechanism configured to releasably secure the trocar assembly within the outer sleeve. The trocar assembly includes a trocar housing defining a pair of openings. The retaining mechanism includes a retaining block, a cam wire moveably positioned relative to the retaining block between a lock position and a release position, a retaining block extension maintaining the cam wire relative to the retaining block, a button member in operable engagement with the cam wire, and a pair of retaining members moveable from a first position received within the first and second openings of the trocar assembly when the cam wire is in the lock position and a second position spaced from the trocar assembly when the cam wire is in the release position. The retaining members each define a cutout having first and second stepped cutout portions and a smooth transition between the first and second stepped cutouts for receiving the cam wire.

In embodiments, the retaining members each include a locking portion, an end surface of the locking portion having first and second chamfered portions. The first and second chamfered portions may be opposite one another. The first and second chamfered portions may facilitate reception of the pair of retaining members within the pair of openings in the trocar housing. The cam wire may include a pair of legs each having an angled portion. The angled portions of the cam wire may be received within the cutouts of the pair of retaining members.

In another aspect, an adapter assembly for connecting a loading unit to a handle assembly includes an outer sleeve, a trocar assembly releasably securable with the outer sleeve, and a retaining mechanism configured to releasably secure the trocar assembly within the outer sleeve. The trocar assembly includes a trocar housing defining a pair of openings. The retaining mechanism includes a retaining block, a cam wire moveably positioned relative to the retaining block between a lock position and a release position, a retaining block extension maintaining the cam wire relative to the retaining block, a button member in operable engagement with the cam wire, and a pair of retaining members moveable from a first position received within the first and second openings of the trocar assembly when the cam wire is in the lock position and a second position spaced from the trocar assembly when the cam wire is in the release position. The retaining members may each include a substantially cylindrical body having a locking portion, an end surface of the locking portion having first and second chamfered portions to facilitate reception of the pair of retaining members within the pair of openings in the trocar housing.

In some embodiments, the first and second chamfered portions are opposite one another. The cam wire may include a pair of legs each having an angled portion. The angled portions of the cam wire may be received within the cutouts of the pair of retaining members.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 7 is a cross-sectional end view the adapter assembly shown in FIG. 2 taken along line 7-7 shown in FIG. 3, with the retainer mechanism in a lock position;

FIG. 7A is an exploded view of the indicated area of detail shown in FIG. 7;

FIG. 8 is a top view of a portion of the adapter assembly including a button member of the retainer mechanism shown in FIG. 5, with a center beam in a first or unflexed condition;

FIG. 21 is side view of the retaining member shown in FIGS. 19 and 20;

FIG. 22 is a cross-sectional end perspective view of an adapter assembly including a retaining mechanism including the retaining member shown in FIGS. 19-21;

FIG. 23 is a cross-sectional top perspective view of the adapter assembly shown in FIG. 22 taken along line 22-22; and FIG. 23A is an exploded view of the indicated area of detail shown in FIG. 23.

DETAILED DESCRIPTION

Figure 1:
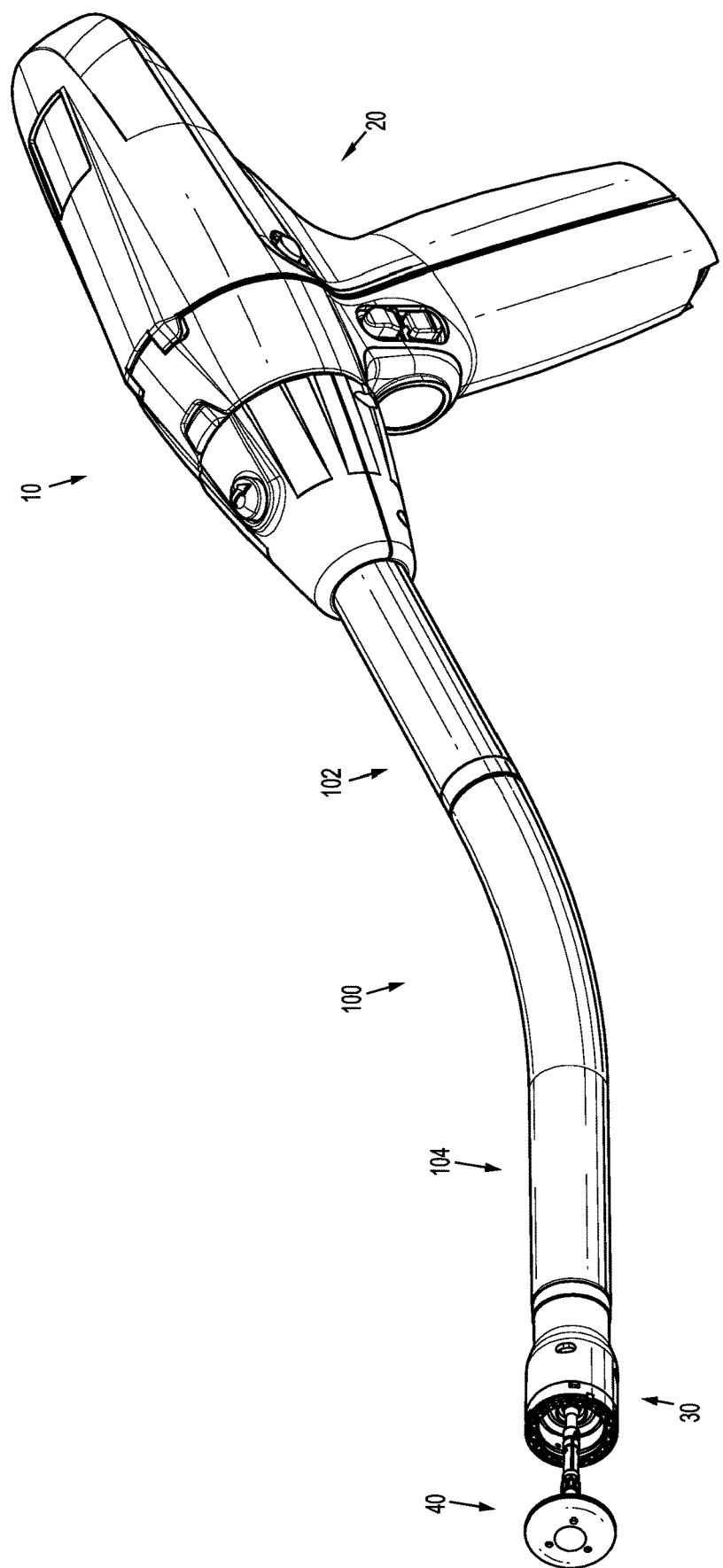
FIG. 1 is a perspective view of a surgical stapling device including an handle assembly and an adapter assembly according to an embodiment of the present disclosure.

Embodiments of the presently disclosed adapter assembly including a retaining mechanism for securing a removable trocar assembly therein will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring initially to FIG. 1, an adapter assembly according to an embodiment of the present disclosure, shown generally as adapter assembly 100, is a component of a surgical stapling device 10. The surgical stapling device 10 further includes a powered handle assembly 20 for actuating a loading unit 30, and an anvil assembly 40 supported relative to the loading unit 30. Although shown and described with reference to surgical stapling device 10, the aspects of the present disclosure may be modified for use with manual surgical stapling devices having various configurations, and with powered surgical stapling devices having alternative configurations. For a detailed description of exemplary surgical stapling devices, please refer to U.S. Pat. Nos. 9,023,014 and 9,055,943, the content of each of which is incorporated by reference herein in its entirety.

Figure 2:
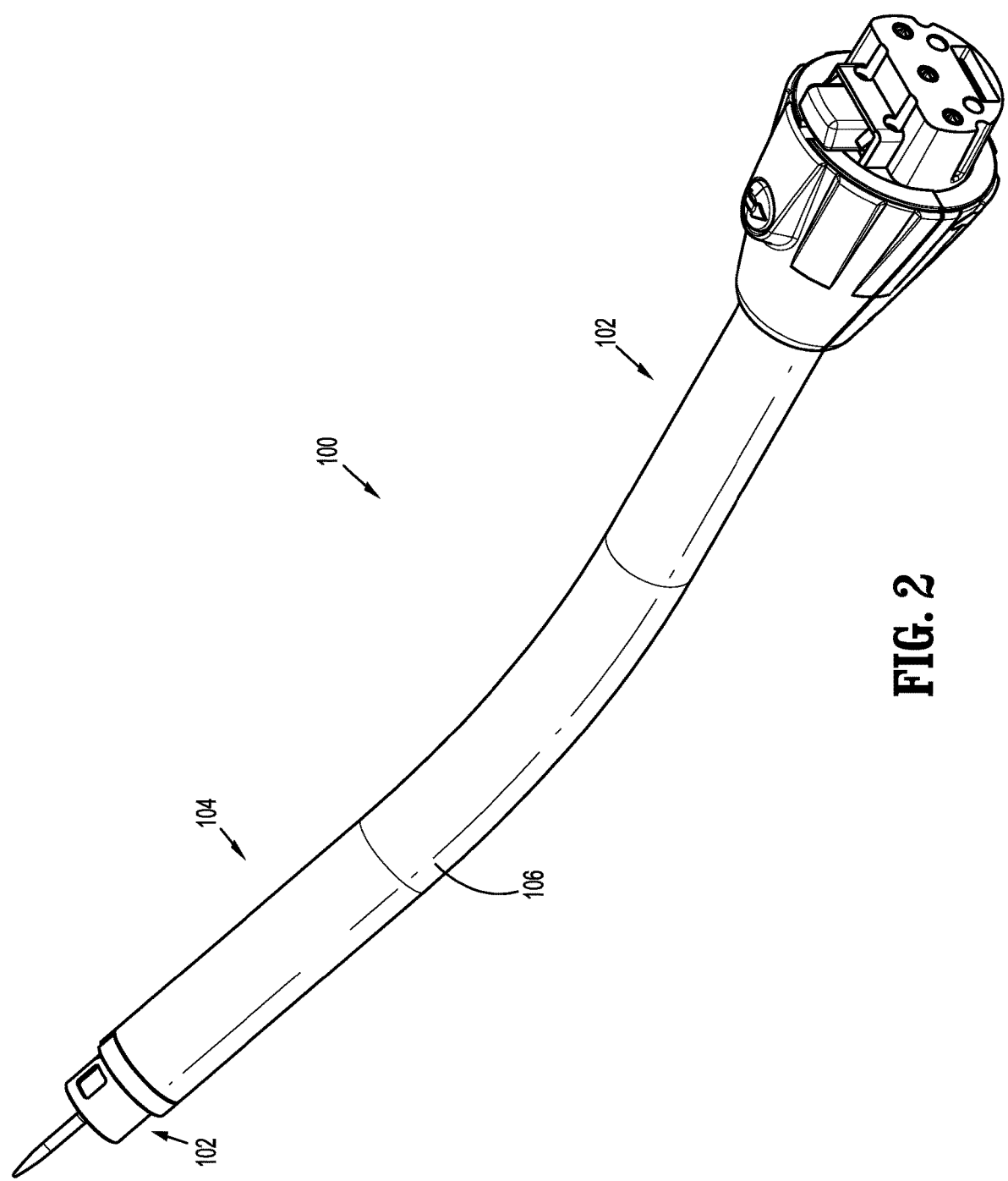
FIG. 2 is a perspective view of the adapter assembly shown in FIG. 1 with a removable trocar assembly extending from a distal portion of the adapter assembly.

With reference to FIG. 2, the adapter assembly 100 includes a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the present disclosure. For a detailed description of an exemplary adapter assembly, please refer to U.S. Pat. No. 10,226,254 ("the '254 patent"), the content of which is incorporated by reference herein in its entirety.

Figure 3:
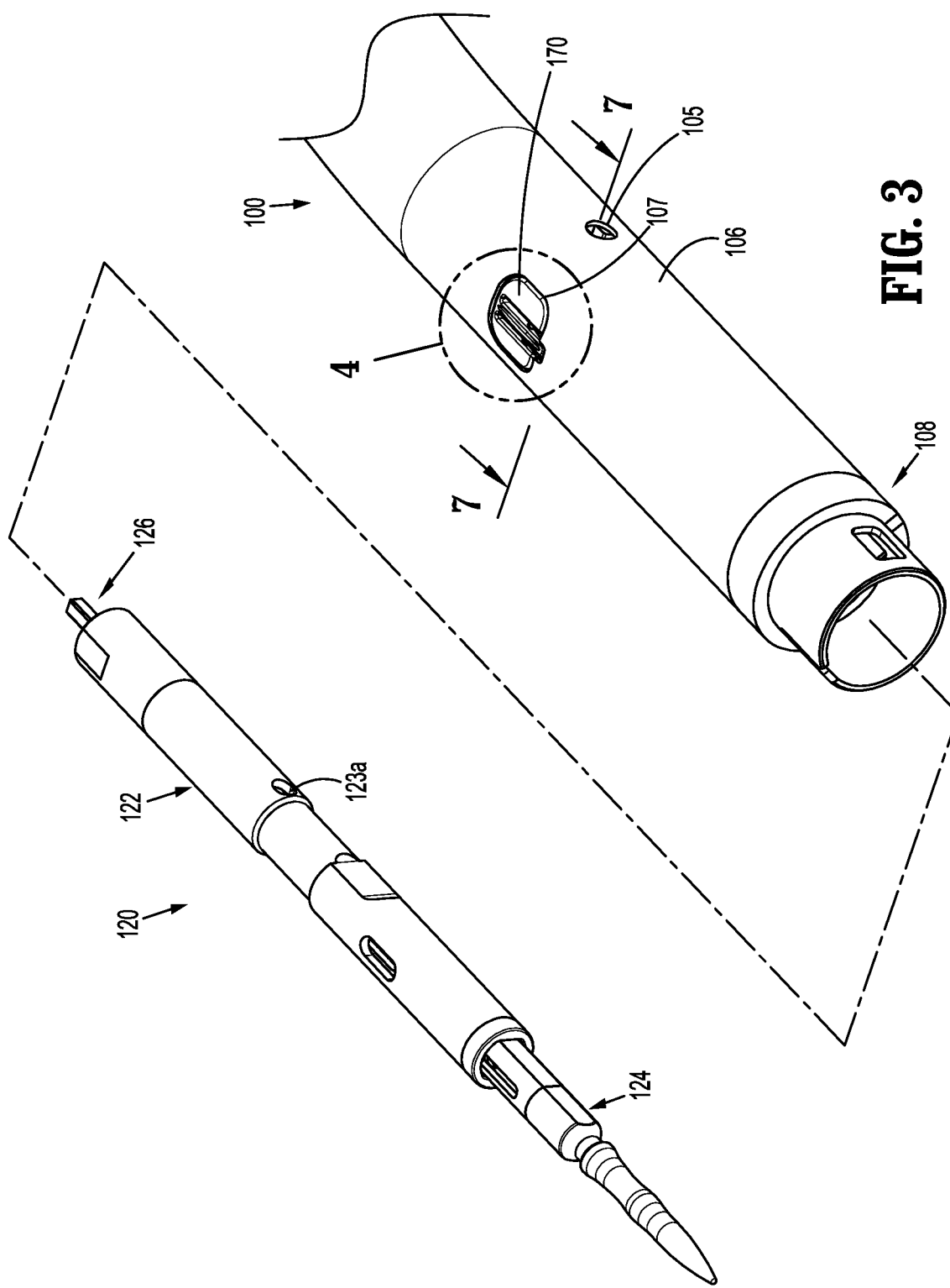
FIG. 3 is a perspective view of the distal portion of the adapter assembly and the removable trocar assembly shown in FIG. 1, with the removable trocar removed from within the adapter assembly.
Figure 4:
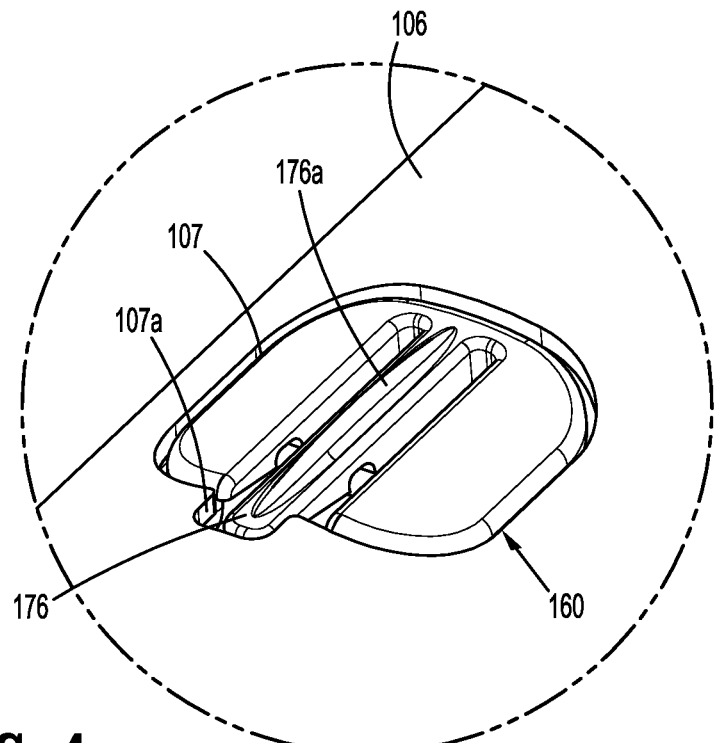
FIG. 4 is an exploded view of the indicated area of detail shown in FIG. 3.

With additional reference to FIGS. 3 and 4, the adapter assembly 100 includes an outer sleeve 106, and a connector housing 108 secured to a distal end of the outer sleeve 106. The connector housing 108 is configured to releasably secure an end effector, e.g., the end effector 30 (FIG. 1), to the adapter assembly 100. The outer sleeve 106 defines a flush port 105 (FIG. 3) and an opening 107 through which a button member 170 of a trocar retaining mechanism 130 is operably disposed. As will be described in further detail below, the outer sleeve 106 further includes an asymmetric cutout 107a (FIG. 4) in communication with the opening 107.

Figure 5:
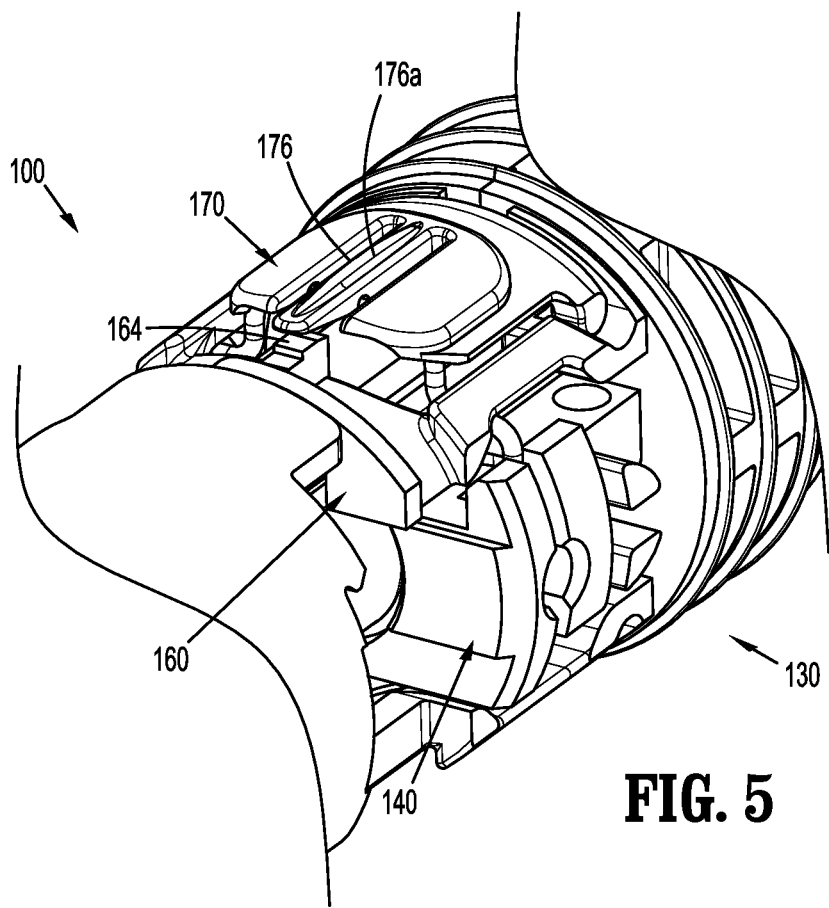
FIG. 5 is a perspective view of the distal portion of the adapter assembly shown in FIG. 2, with an outer sleeve removed to expose a retaining mechanism.

With additional reference to FIG. 5, the adapter assembly 100 further includes a trocar assembly 120 (FIG. 3), and a retaining mechanism 130 releasably securing the trocar assembly 120 relative to the outer sleeve 106 (FIG. 3) of the adapter assembly 100. The trocar assembly 120 will only be described to the extent necessary to fully describe the aspects of the present disclosure. For a detail description of the structure and function of an exemplary trocar assembly, please refer to the '254 patent, the content of which was previously incorporated by reference herein in its entirety.

With particular reference to FIG. 3, the trocar assembly 120 of the adapter assembly 100 (FIG. 2) includes a trocar housing 122, a trocar member 124 slidably disposed within the trocar housing 122, and a drive screw 126 operably received within the trocar member 124 for axially moving the trocar member 124 relative to the trocar housing 122. The trocar housing 122 defines first and second locking openings 123a, 123b (FIG. 7) for receiving respective locking portions 182a, 182b of first and second retainer members 180a, 180b (FIG. 6) of a retaining mechanism 130 of the adapter assembly 100.

Turning briefly to FIG. 7, the retaining mechanism 130 of the adapter assembly 100 is disposed between first and second drive members 110a, 110b, 112a, 112b of respective inner and outer drive assemblies 110, 112. The first and second drive assemblies 110, 112 are operably connected to first and second drive shafts (not shown) in a proximal portion 102 of the adapter assembly 100 for effecting operation of an end effector, e.g., the end effector 30 (FIG. 1), to perform first and second functions. More particularly, the first and second drive members 110a, 110b, 112a, 112b of the respective first and second drive assemblies 110, 112 are configured for longitudinal movement within the distal portion 104 of the adapter assembly 100. In embodiments, advancement of the first drive assembly 110 effects tissue stapling, and advancement of the second drive assembly 112 effects tissue cutting.

The first and second drive assemblies 110, 112 will only be described to the extent necessary to fully disclose the aspects of the present disclosure. For a detailed description of exemplary drive assemblies, please refer to the '254 patent, the content of which was previously incorporated herein.

Figure 6:
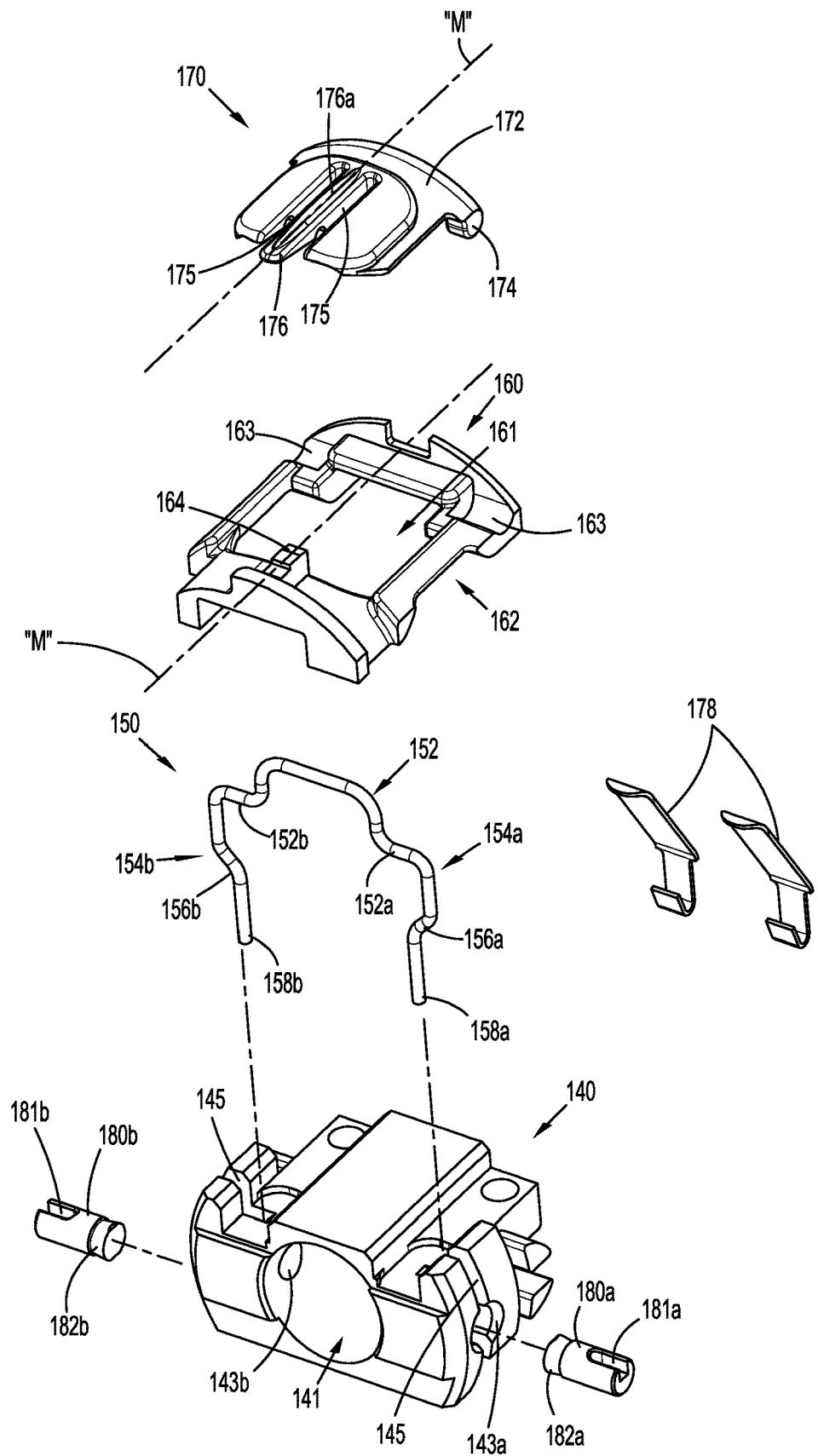
FIG. 6 is a side perspective view of the retaining mechanism shown in FIG. 5, with components separated.

With reference now to FIGS. 5 and 6, the retaining mechanism 130 of the adapter assembly 100 includes a retaining block 140, a cam wire 150 (FIG. 6) supported by the retaining block 140, a retaining block extension 160 for maintaining the cam wire 150 relative the retaining block 140, a button member 170 in operable engagement with the cam wire 150 and pivotally supported relative to the retaining block 140, and first and second retainer members 180a, 180b (FIG. 6) supported by the cam wire 150 within the retaining block 140.

With particular reference to FIG. 6, the retaining block 140 of the retaining mechanism 130 defines a central opening 141 for receiving the trocar assembly 120 (FIG. 3), first and second opposed cylindrical openings 143a, 143b in communication with the central opening 141 for receiving the respective first and second retainer members 180a, 180b, and a channel or slot 145 extending about a perimeter of the retaining block 140 and through the first and second cylindrical openings 143a, 143b in the retaining block 140 for receiving the cam wire 150. The first and second retainer members 180a, 180b of the retaining mechanism 130 are supported within the first and second cylindrical openings 143a, 143b of the retaining block 140 by the cam wire 150 and are configured to be received within first and second locking openings 123a, 123b of the trocar housing 122 of the trocar assembly 120 when the trocar assembly 120 is fully received within the distal portion 104 (FIG. 2) of the adapter assembly 100.

The cam wire 150 of the retaining mechanism 130 includes a substantially U-shaped member having a backspan 152, and first and second legs 154a, 154b extending from the backspan 152. The backspan 152 includes a button engagement portion 152a and a pair of shoulders portions 152b on either side of the button engagement portion 152a. Each of the first and second legs 154a, 154b includes an opposed angled section 156a, 156b. The cam wire 150 is received within the channel 145 of the retaining block 140. As will be described in further detail below, the cam wire 150 is moveable between a first or lock position (FIG. 8) when the button member 170 is in an initial or non-depressed position, and a second or release position when the button member 170 is depressed.

With continued reference to FIG. 6, the retaining block extension 160 includes a substantially rectangular frame 162 defining an opening 161 and a pair semi-cylindrical recesses 163. First and second pivot portions 174 (only one shown) of the button member 170 are pivotally supported within the semi-cylindrical recesses 163 in the frame 162 and a body portion 172 of the button member is disposed within the opening 161. The frame 162 includes a pair of stop surfaces 162a (FIG. 7) for engaging the shoulder portions 152b of the backspan 152 of the cam wire 150, and a stop member, e.g., a stop tab 164, along a midline "m" of the frame 162 for inhibiting depression of the button member 170.

The button member 170 of the retaining mechanism 130 of the adapter assembly 100 (FIG. 2) includes the body portion 172 configured for operable engagement by a user, and the pair of pivot portions 174 configured for reception within the pair of semi-cylindrical recesses 163 of the retaining block extension 160. The button member 170 is configured for operable engagement with the engagement portion 152a of the backspan 152 of the cam wire 150. In embodiments, the cam wire 150 is secured to the button member 170. For example, and as shown, the body portion 172 of the button member 170 defines a cavity 171 (FIG. 7A) in with the engagement portion 152a of the back span 152 is retained through friction fit. Alternatively, the backspan 152 is secured within the cavity 171 with mechanically fasteners, bonding, welding, adhesives, or in any other suitable manner. The retaining mechanism 130 may include a biasing member, e.g., leaf springs 178 for bias the cam wire 150 outwardly to the first position, and/or the button member 170 outwardly to the non-depressed position (FIG. 7).

The button member 170 of the trocar retaining mechanism 130 further includes a center beam 176, and defines a relief 175 on either side of the center beam 176. The center beam 176 includes a rib 176a, or is otherwise configured for engagement by a user. The center beam 176 and reliefs 175 are configured such that the center beam 176 may be flexed away from a midline "M" of the button member 170. More particularly, the center beam 176 of the button member 170 is configured to align with the stop tab 164 of the retaining block extension 160 when the center beam 176 is in an initial or unflexed condition. In this manner, the center beam 176 of the button member 170 prevents the button member 170 from being depressed. As will be described in further detail below, flexing of the center beam 176 away from the midline "M" of the button member 170 moves the center beam 176 out of alignment with the stop tab 164 of the retaining block extension 160, thereby permitting depression of the button member 170. The reliefs 175 in the button member 170 may also facilitate flushing and cleaning of the adapter assembly 100 (FIG. 2)

The first and second retaining members 180a, 180b of the retaining mechanism 130 form substantially cylindrical bodies 182a, 182b. The first and second retaining members 180a, 180b are supported on the angled portions 156a, 156b of the respective first and second legs 154a, 154b of the cam wire 150. In embodiments, and as shown the first and second retaining members 180a, 180b form a wedge-shaped configured to be received within wedge-shaped first and second locking openings 123a, 123b in the trocar housing 122 of the trocar assembly 120. The first and second retaining members 180a, 180b may include an inclined inner surface (not shown) to facilitate receipt of the trocar assembly 120 through the retaining block 140.

The first and second retaining members 180a, 180b each define a stepped opening 181a, 18ab through which the respective angled portion 156a, 156b of the cam wire 150 are received. The cam wire 150 and the stepped openings 181a, 181b of the respective first and second retaining members 180a, 180b are configured such that when the cam wire 150 is in the first position, the first and second retaining members 180a, 180b extend from within the retaining block 140 into the central passage 141. In this manner, when a trocar assembly 120 is fully seated within the distal portion 104 (FIG. 2) of the adapter assembly 100, the first and second retaining members 180a, 180b are received within the respective first and second locking openings 123a, 123b (FIG. 7) of the trocar housing 122 of the trocar assembly 120. Conversely, when the cam wire 150 is in the second or release position, the first and second retainer members 180a, 180b are retracted from within the central opening 141 of the retaining block 140 to permit insertion and/or removal of the trocar assembly 120 from the distal portion 104 of the adapter assembly 100.

With reference now to FIGS. 7-8, the retaining mechanism 130 of the adapter assembly 100 is shown in a first or lock configuration, with the trocar assembly 120 securely received within the distal portion 104 of the adapter assembly 100. In the lock configuration, the cam wire 150 of the retaining mechanism 130, secured to the button member 170, is biased to the first position by the leaf springs 178 (FIG. 6). In the first position, the shoulder portions 152b of the backspan 152 of the cam wire 150 engaging the stop surface 162a of the retaining block extension 160. As noted above, when the cam wire 150 is in the first position, and the trocar assembly 120 is fully seated within the distal portion 104 (FIG. 2) of the adapter assembly 100, the first and second retainer members 180a, 180b are received within the respective first and second locking openings 123a, 123b in the trocar housing 122 of the trocar assembly 120.

With continued reference to FIGS. 7-8, the center beam 176 of the button member 170 of the retaining mechanism 130 is shown in the first or unflexed position. In the unflexed position, the center beam 176 aligns with the midline "M" of the button member 170. When aligned with the midline "M", the center beam 176 engages the stop tab 164 of the retaining block extension 160 which is also aligned with the midline "M" of the button member 170, thereby preventing the button member 170 from being depressed.

Figure 9:
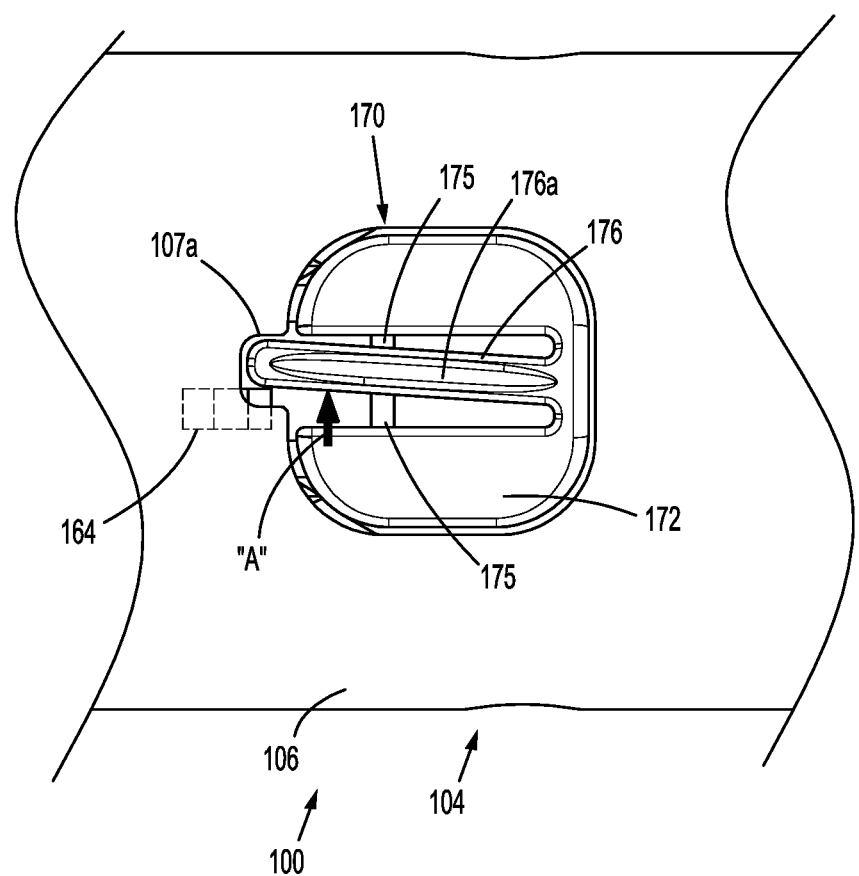
FIG. 9 is the top view shown in FIG. 9 with the center beam of the button member in a second of flexed condition.

Turning to FIG. 9, following use of the adapter assembly 100, or to otherwise remove the trocar assembly 120 from the distal portion 104 of the adapter assembly 100, the rib 176a of the center beam 176 of the button member 170 of the retaining mechanism 130 is moved off-center, or away from the midline "M" of the button member 170 to the flexed position, as indicated by arrow "A", to move the center beam 176 of the button member 170 out of alignment with the stop tab 164 of the retaining block extension 160. As noted above, when the center beam 176 of the button member 170 is misaligned with the stop tab 164 of the retaining block extension 160 the stop tab 164 no longer obstructs or inhibits the button member 170 from being depressed.

Figure 10:
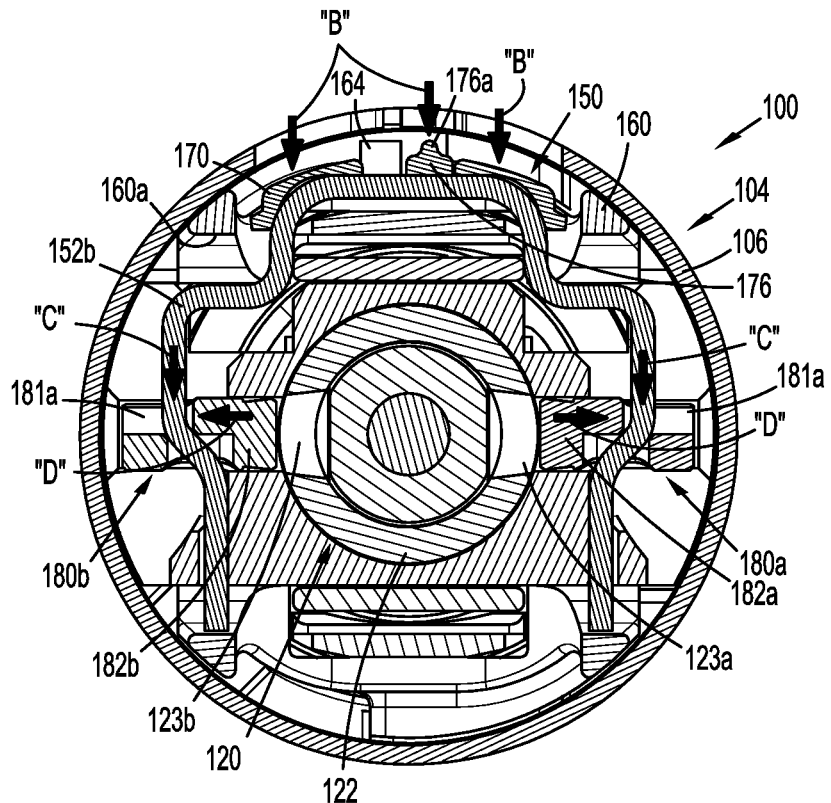
FIG. 10 is the cross-sectional end view of the adapter assembly shown in FIG. 7, with the retainer mechanism in a release position.
Figure 11:
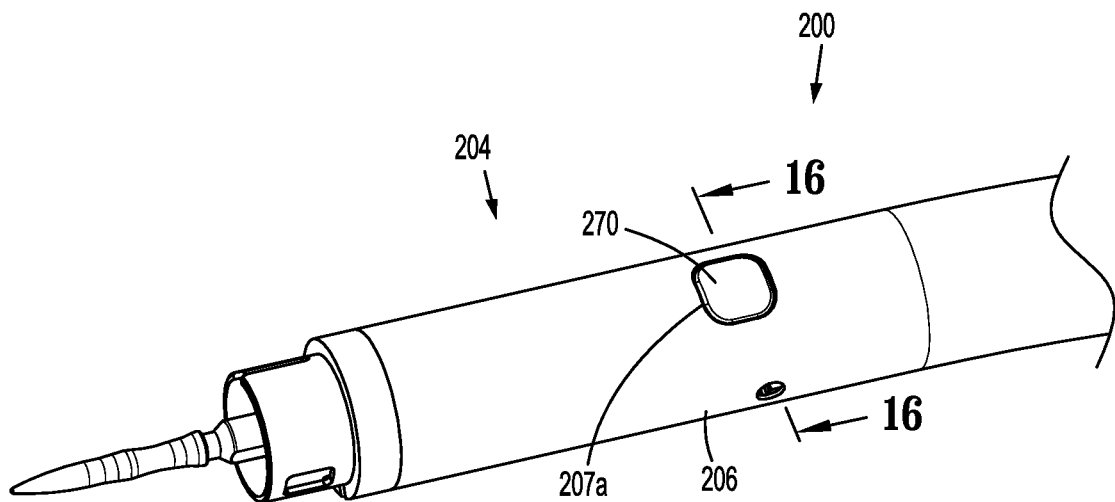
FIG. 11 is a perspective view of a distal portion of an adapter assembly according to another embodiment of the present disclosure.
Figure 12:
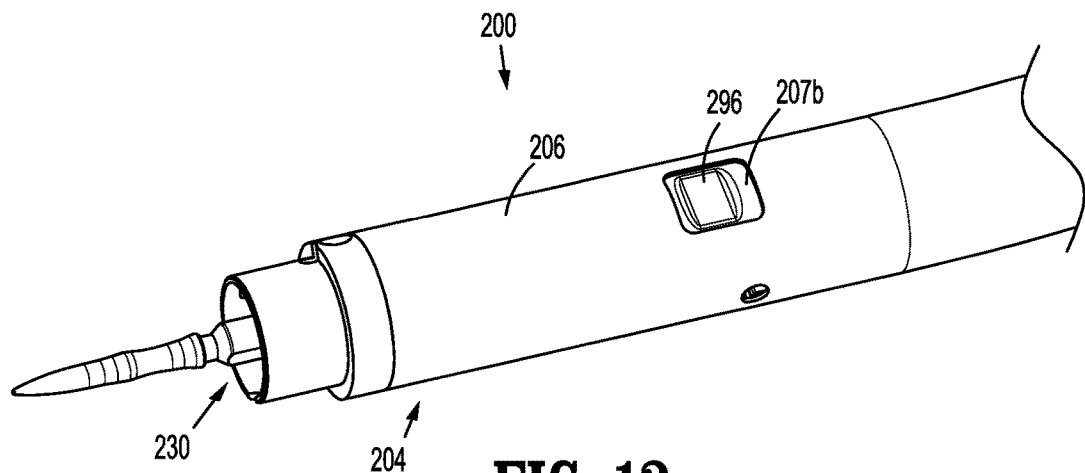
FIG. 12 is another perspective view of the distal portion of the adapter assembly shown in FIG. 11.

With reference to FIG. 10, with the center beam 176 of the button member 170 in the flexed position, the button member 170 is able to be depressed, as indicated by arrows "B". Depression of the button member 170 causes the cam wire 150 to move from its first position (FIG. 7) to its second position, as indicated by arrows "C". As the cam wire 150 moves to the second position, engagement of the angled portions 156a, 156b of the first and second legs 154a, 154b, respectively, with the respective first and second retainer members 180a, 180b cause the first and second retainer members 180a, 180b to move radially outward, as indicated by arrows "D". Radial outward movement of the first and second retaining members 180a, 180b withdraws the first and second retaining members 180a, 180b from within the respective first and second locking openings 123a, 123b of the trocar housing 122 of the trocar assembly 120 to permit removal of the trocar assembly 120 from within the distal portion 104 of the adapter assembly 100 (FIG. 2).

Figure 13:
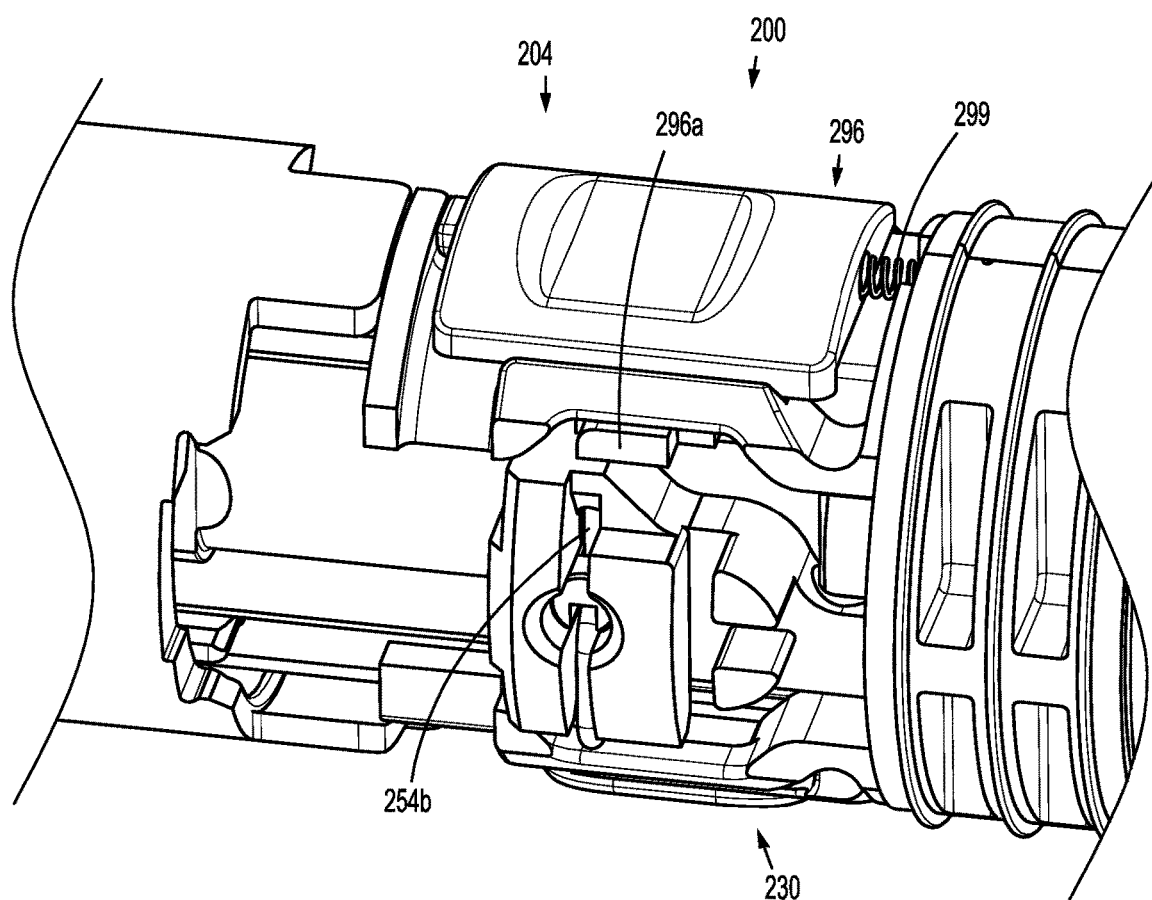
FIG. 13 is a perspective view of the distal portion of the adapter assembly shown in FIG. 11, with an outer sleeve removed to expose a retaining mechanism.

With reference now to FIGS. 11-18, another embodiment of a retaining mechanism according to the present disclosure is shown generally as retaining mechanism 230 (FIG. 13). The retaining mechanism 230 is substantially similar to retaining mechanism 130 described hereinabove and will only be described in detail with regards to the differences therebetween. The retaining mechanism 230 releasably secures a trocar assembly 220 within a distal portion 204 of an adapter assembly 200. The trocar assembly 220 includes a trocar housing 222 defining first and second locking openings 223a, 223b for receiving retaining members 280a, 280b (FIG. 16), respectively, of the retaining mechanism 230.

Figure 14:
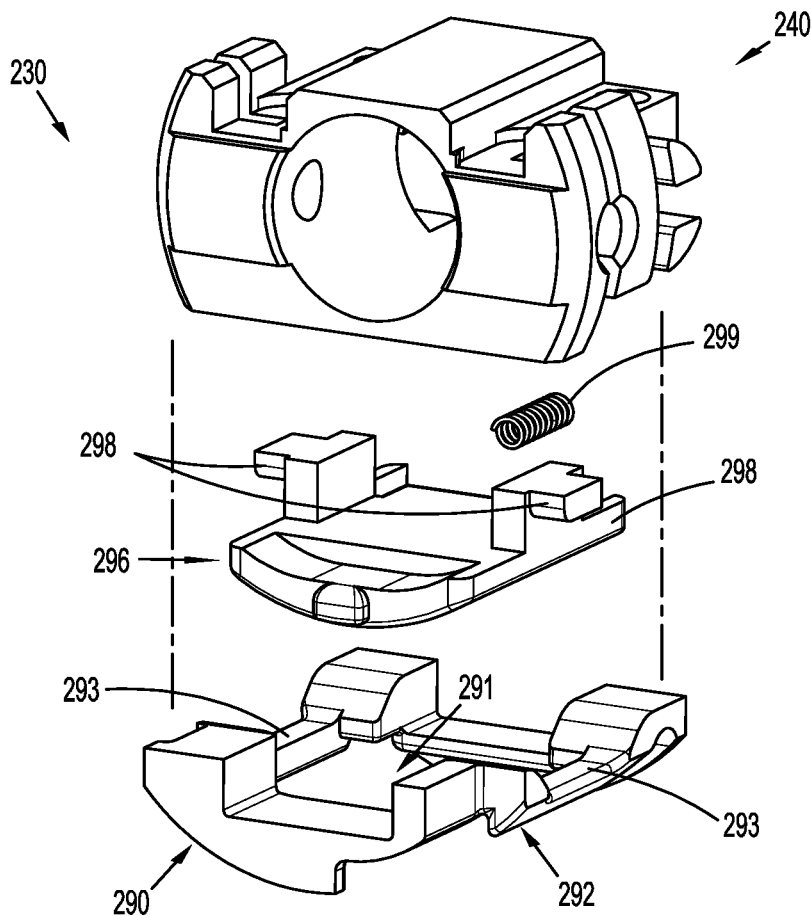
FIG. 14 is a side perspective view of the retaining mechanism shown in FIG. 13, with components separated.

With particular reference to FIGS. 13 and 14, the retaining mechanism 230 of the access assembly 200 includes a retaining block 240 (FIG. 13), a cam wire 250 (FIG. 16) moveably positioned relative to the retaining block 240, an upper retaining block extension 260 securing the cam wire 250 relative to the retaining block 240, a button member 270 pivotally supported by the upper retaining block 260 and in operable engagement with the cam wire 250, first and second retaining members 280a, 280b in operable engagement with the cam wire 250 and moveably disposed within the retaining block 230, a lower retaining block extension 290 disposed opposite the upper retaining block 260 in engagement with the retaining block 240, and a sliding button member 296 slidably supported on the lower retaining block extension 290.

The retaining block 240, cam wire 250, and first and second retaining members 280a, 280b of the retaining mechanism 230 of the access assembly 200 are substantially similar to the retaining block 140, cam wire 150, and first and second retaining members 180a, 180b described above. The upper retaining block extension 260 and the button member 270 are also substantially similar to the retaining block extension 160 and the button member 170. The button member 270 of the retaining mechanism 230 is accessible through a first opening 207 (FIG. 11) in an outer sleeve 206 of the adapter assembly 200. The sliding button member 296 is accessible through a second opening 207b (FIG. 12) in the outer sleeve 206.

Figure 15:
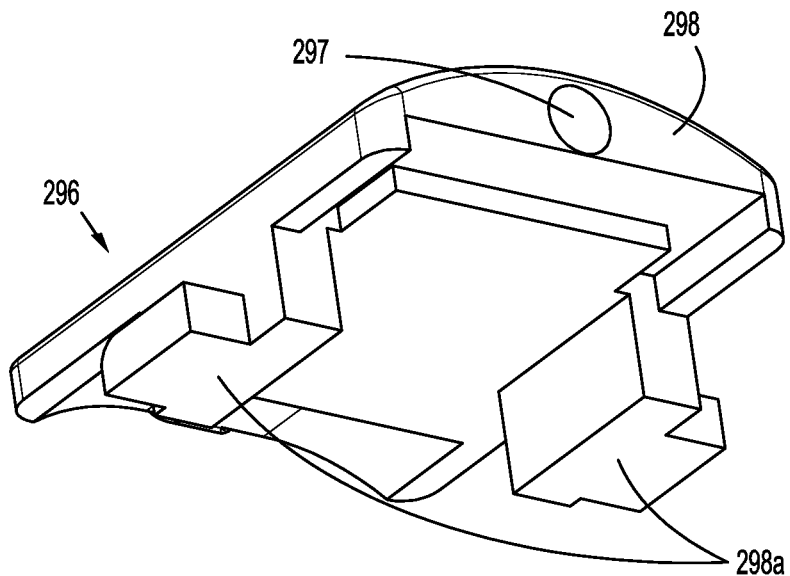
FIG. 15 is a perspective view of a lower retaining block extension of the retaining mechanism shown in FIG. 13.

With particular reference to FIGS. 14 and 15, the lower retaining block extension 290 of the retaining mechanism 230 includes a substantially rectangular frame 292 defining an opening 291 for receiving the sliding button member 296. A pair of cutouts 293 in the frame 292 support a pair of stop members 298a of the sliding button member 296. The lower retaining block extension 290 is received within the outer sleeve 206 (FIG. 16) of the adapter assembly in engagement with the retaining block 240 and opposite the upper retaining block extension 260.

The sliding button member 296 of the retaining mechanism 290 includes a body portion 298 configured for operable engagement by a user, and the pair of stop members 298a extending outwardly from the body portion 298. The stop members 298a ride within the cutouts 293 of the lower retaining block extension 290. The sliding button member 296 is moveable between a first or distal position (FIG. 13) in which the stop members 298a of the sliding button member 296 are aligned with free ends 258a, 258b (FIG. 16) of legs 254a, 254b, respectively, of the cam wire 250 and a second or proximal position (FIG. 17) in which the stop members 298a are spaced from the free ends 258a, 258b of the legs 254a, 254b, respectively, of the cam wire 250.

A cylindrical recesses 297 (FIG. 15) in an end for the sliding button member 296 of the retaining assembly 230 is configured to receive a biasing member, e.g., a coil spring 299 (FIG. 14) for biasing the sliding button member 296 in a first direction, e.g., distally, as shown, to the distal position. The sliding button member 296 is accessible through the second opening 207b (FIG. 12) in the outer sleeve 206 of the adapter assembly 200.

Figure 16:
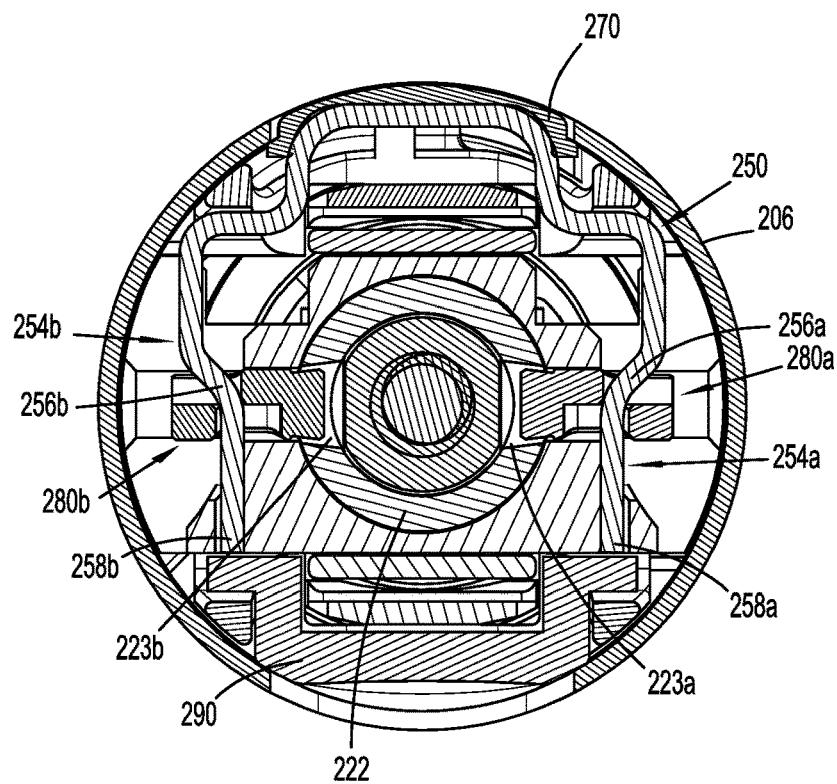
FIG. 16 is a cross-sectional end view of the adapter assembly shown in FIG. 11 taken along line 16-16.

With particular reference to FIG. 16, the retaining mechanism 230 is shown in a first or lock position with the cam wire 250 in a first position and the sliding button member 296 in the distal position. The sliding button member 296 is maintained in the distal position by the coil spring 299. As described above, when the sliding button member 296 of the retaining mechanism 230 is in the proximal position, the stop members 298a of the sliding button member 298 align with the free ends 258a, 258b of the legs 254a, 254b, respectively, of the cam wire 250 to prevent movement of the cam wire 250 to the second position.

Figure 17:
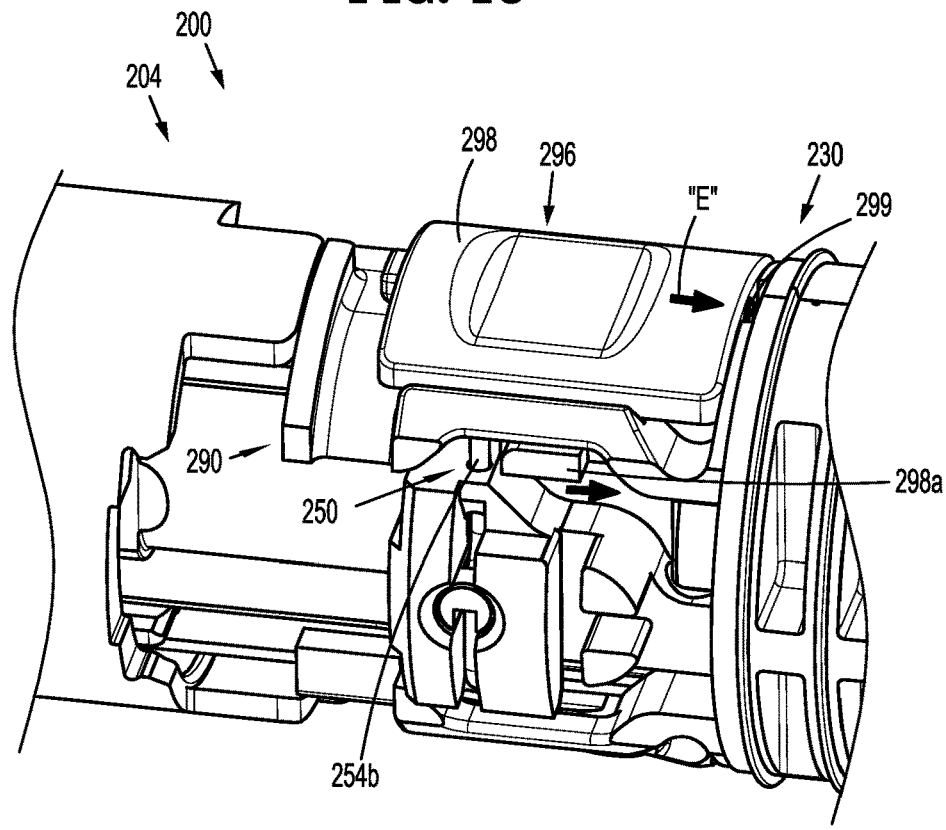
FIG. 17 is the perspective view of the distal portion of the adapter assembly shown in FIG. 13, with a sliding button member of the retaining mechanism shown in FIG. 13 in a proximal position.
Figure 18:
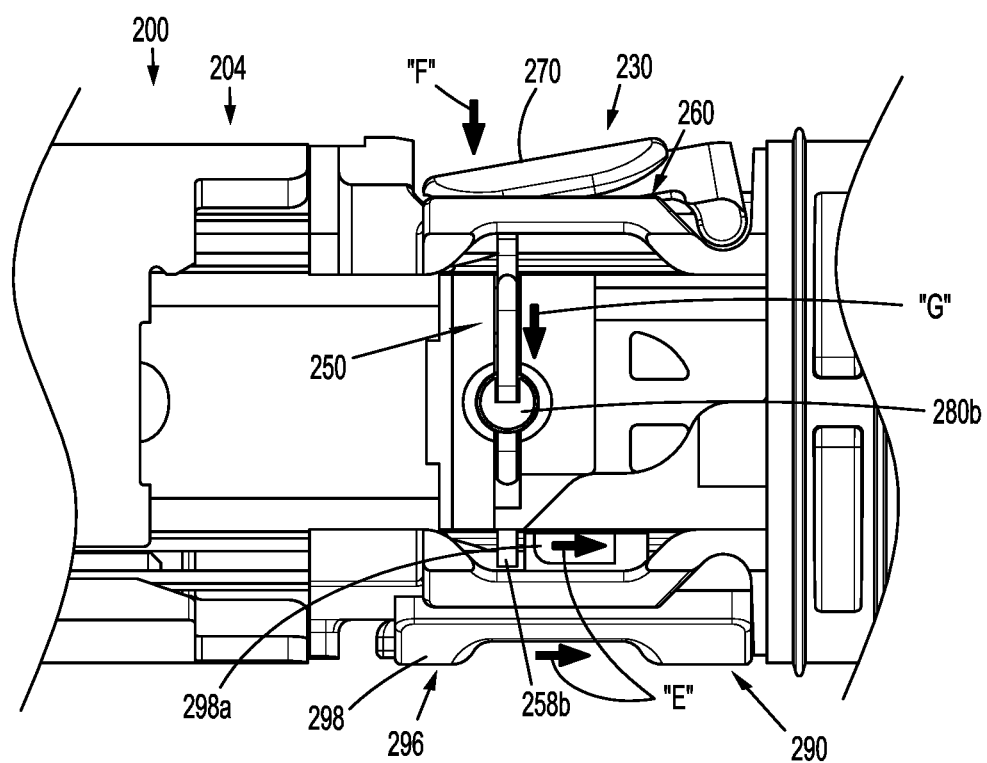
FIG. 18 is a side view of the retaining mechanism shown in FIG. 17, with the sliding button member in the proximal position and the button member in a depressed condition.

Turning to FIGS. 17 and 18, subsequent to use, or at any time the trocar assembly 230 is desired to be removed from the distal portion 204 of the adapter assembly 200, the sliding button member 296 is moved proximally, against the bias of the coil spring 299, as indicated by arrows "E". Proximal movement of the sliding button member 296 moves the stop members 298a of the sliding button member 296 out of engagement with the free ends 258a, 258b (FIG. 16) of the legs 254a, 254b, respectively, of the cam wire 250.

With the stop members 298a of the sliding button member 296 no longer preventing movement of the cam wire 250 to the second position, the button member 270 may be depressed, as indicated by arrow "F" to cause the cam wire 250 to move to the second position, as indicated by arrows "G". As discussed in detail above with respect to retaining mechanism 130, as the cam wire 250 moves to the second position, the retaining members 280a, 280b (FIG. 16) move radially outward from within first and second locking openings 223a, 223b of a trocar housing 232 of the trocar assembly 230 to release the trocar assembly 230 from within the distal portion 204 of the adapter assembly 200, and permit removal of the trocar assembly 230 from within the adapter assembly 200.

FIGS. 19-23 illustrate another embodiment of a retaining mechanism of the disclosure shown generally as retaining mechanism 330. (FIG. 22). The retaining mechanism 330 is substantially similar to retaining mechanism 130 and 230 described hereinabove, and will only be described as relates to the differences therebetween.

Figure 19:
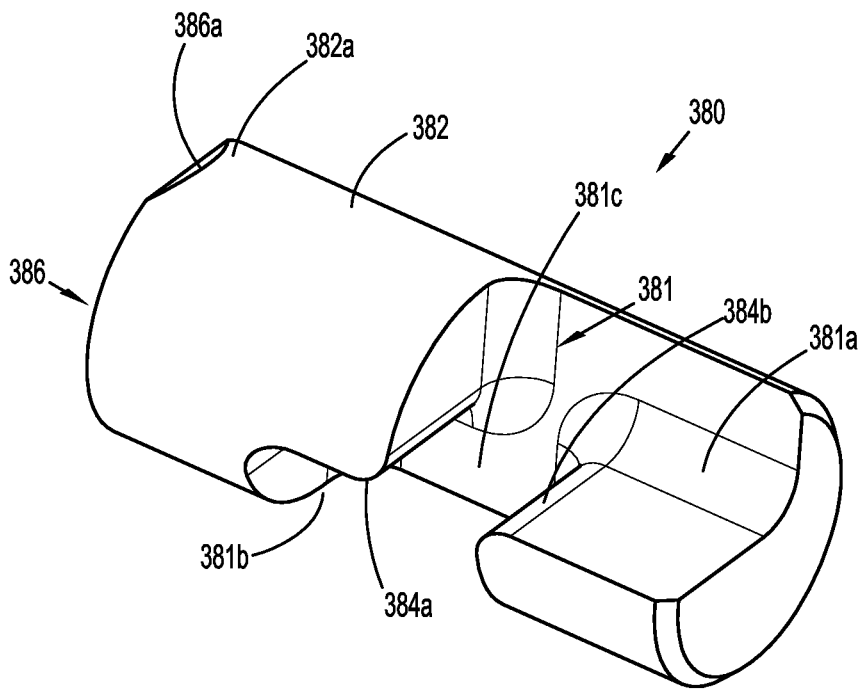
FIG. 19 is a first perspective view a retaining member according to an embodiment of the present disclosure.
Figure 20:
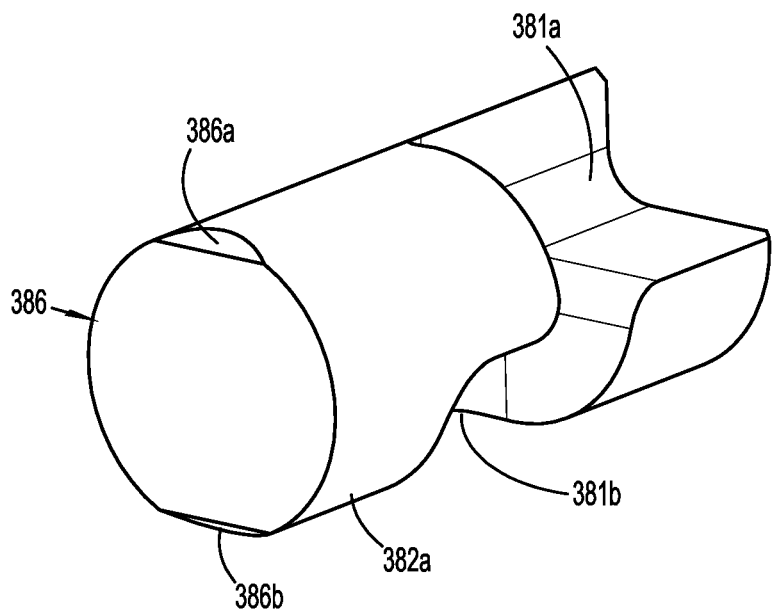
FIG. 20 is a second perspective view of the retaining member shown in FIG. 19.

FIGS. 19-21 illustrate an exemplary retaining member 380 of retaining mechanism 330 (FIG. 22). The retaining member 380 includes a substantially cylindrical body 382 defining a cutout 381. The cutout 381 includes a first or upper cutout portion 381a, and a second or lower cutout portion 381b. The first and second portions 381a, 381b are staggered relative to each other and define an opening 381c therebetween. The inner surface 384 of the cylindrical body 382 is smooth and includes rounded transitions to accommodate passage of angled portions 356a, 356b (FIG. 22) of legs 354a, 354b, respectively, of a cam wire 350. For example, the first and second surface portions 384a, 384b of the inner surface 384 (FIG. 19) bounding the opening 381c between the upper and lower cutout portions 381a, 381b of the cutout 381. In embodiments, the inner surface 384 may be contoured or otherwise formed to accommodate the smooth passage of the cam wire 350.

The cutout 381 in the retaining member 380 may be formed using a mill. More particularly, the upper and lower cutout portions 381a, 381b may be milled entirely from a first side of the cylindrical body 382. In this manner, the cutout 381 in the retaining member 380 may be formed in one pass, thereby reducing manufacturing time and costs. Milling the cutout 381 from a single side also reduces the likelihood of burrs or jagged edges forming within the cutout 381 of the retaining member 380.

The cylindrical body 382 of the retaining member 380 includes a locking portion 382a configured for selective reception within locking openings 323a, 323b (FIG. 22) in a trocar housing 322 of a trocar assembly 320. An end surface 386 of the locking portion 382a of the retaining member 380 includes upper and lower chamfered surfaces 386a, 386b. The upper and lower chamfered surfaces 386a, 386b facilitated alignment of the retaining member 380 with the locking opening 323a, 323b of the trocar housing 322 of the trocar assembly 320.

Chamfering two areas of the end surface 386, e.g., upper and lower chamfered surfaces 386a, 386b, of the retaining member 380, as opposed to chamfering the entire outer perimeter of the end surface 386 reduces the likelihood that the chamfered outer edge of the retaining member 380 would engage the trocar housing 322 of the trocar assembly 320, thereby only partially locking the trocar assembly 320 with an adapter assembly 300.

With reference to FIG. 23, the retaining member 380 engages the trocar housing 322 along the sides of the locking portion 382a of the cylindrical body 382. By positioning the upper and lower chamfered surfaces 386a, 386b (FIG. 20) on the upper and lower portions of the end surface 386 of the locking portion 382a, a full diameter of the cylindrical body 382 of the retaining member 380 engages the trocar housing 322 of the trocar assembly 320 to ensure secure connection.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described.

What is claimed is:

1. An adapter assembly for connecting a loading unit to a handle assembly, the adapter assembly comprising:
    an outer sleeve;
    a trocar assembly releasably securable with the outer sleeve, the trocar assembly including a trocar housing defining a pair of openings; and
    a retaining mechanism configured to releasably secure the trocar assembly within the outer sleeve, the retaining mechanism including a retaining block, a cam wire moveably positioned relative to the retaining block between a lock position and a release position, a retaining block extension maintaining the cam wire relative to the retaining block, a button member in operable engagement with the cam wire, and a pair of retaining members moveable from a first position received within the first and second openings of the trocar assembly when the cam wire is in the lock position and a second position spaced from the trocar assembly when the cam wire is in the release position, wherein each retaining member of the pair of retaining members defines a cutout having first and second stepped cutout portions and a smooth transition between the first and second stepped cutouts for receiving the cam wire.

2. The adapter assembly of claim 1, wherein each retaining member of the pair of retaining members includes a locking portion, an end surface of the locking portion having first and second chamfered portions.

3. The adapter assembly of claim 2, wherein the first and second chamfered portions are opposite one another.

4. The adapter assembly of claim 2, wherein the first and second chamfered portions facilitate reception of the pair of retaining members within the pair of openings in the trocar housing.

5. The adapter assembly of claim 1, wherein the cam wire includes a pair of legs, each leg of the pair of legs having an angled portion.

6. The adapter assembly of claim 5, wherein the angled portions of the cam wire are received within the cutouts of the pair of retaining members.

7. An adapter assembly for connecting a loading unit to a handle assembly, the adapter assembly comprising:
    an outer sleeve;
    a trocar assembly releasably securable with the outer sleeve, the trocar assembly including a trocar housing defining a pair of openings; and
    a retaining mechanism configured to releasably secure the trocar assembly within the outer sleeve, the retaining mechanism including a retaining block, a cam wire moveably positioned relative to the retaining block between a lock position and a release position, a retaining block extension maintaining the cam wire relative to the retaining block, a button member in operable engagement with the cam wire, and a pair of retaining members moveable from a first position received within the first and second openings of the trocar assembly when the cam wire is in the lock position, and a second position spaced from the trocar assembly when the cam wire is in the release position, wherein each retaining member of the pair of retaining members includes a substantially cylindrical body having a locking portion, an end surface of the locking portion having first and second chamfered portions to facilitate reception of the pair of retaining members within the pair of openings in the trocar housing.

8. The adapter assembly of claim 7, wherein the first and second chamfered portions are opposite one another.

9. The adapter assembly of claim 7, wherein the cam wire includes a pair of legs, each leg of the pair of legs having an angled portion.

10. The adapter assembly of claim 9, wherein the angled portions of the cam wire are received within the cutouts of the pair of retaining members.

* * * * *